(12) United States Patent
Tucker

(10) Patent No.: US 7,341,056 B1
(45) Date of Patent: Mar. 11, 2008

(54) PORTABLE OXYGEN SUPPLY UNIT

(75) Inventor: Daniel R. Tucker, Springfield, MO (US)

(73) Assignee: The Big Ox, L.L.C., Springfield, MO (US)

( * ) Notice: Subject to any disclaimer, the term of this patent is extended or adjusted under 35 U.S.C. 154(b) by 447 days.

(21) Appl. No.: 11/136,856

(22) Filed: May 25, 2005

(51) Int. Cl.
*A61M 11/00* (2006.01)

(52) U.S. Cl. .......................... 128/200.14; 128/200.23; 128/200.21; 222/402.13; 222/402.21; 222/402.15; 239/338

(58) Field of Classification Search ........... 128/200.14, 128/200.18, 200.22, 200.24, 200.23, 203.15, 128/203.23, 204.24, 204.25, 204.27, 205.24, 128/200.11; 222/94.95, 136, 145.5, 402.23, 222/402.18, 402.25, 402.11–402.15, 153.12, 222/402.22, 402.24, 518, 153.11; 215/4, 215/228, 201; 251/61.1, 244, 291, 342; 239/270, 525, 569, 317, 338; 137/588

See application file for complete search history.

(56) References Cited

U.S. PATENT DOCUMENTS

| | | | |
|---|---|---|---|
| 2,087,119 A | 7/1937 | Rosenow et al. | 128/205.25 |
| 2,510,712 A | 6/1950 | Olowinski | 128/203.12 |
| 3,019,788 A | 2/1962 | Hughes | 128/205.24 |
| 3,151,618 A * | 10/1964 | Wakeman | 128/200.23 |
| 3,186,407 A | 6/1965 | Morrison | 128/205.24 |
| 3,326,231 A | 6/1967 | Hogg | 137/318 |
| 3,625,403 A * | 12/1971 | Rousselot | 222/635 |
| 4,068,681 A * | 1/1978 | McNair et al. | 137/588 |
| 4,077,549 A * | 3/1978 | Beard | 222/321.8 |
| 4,230,243 A * | 10/1980 | Spitzer et al. | 222/402.18 |
| 4,427,134 A * | 1/1984 | Almouli | 222/153.11 |
| 4,513,889 A * | 4/1985 | Beard | 222/153.07 |
| 4,582,054 A | 4/1986 | Ferrer | 128/200.23 |
| 4,637,387 A | 1/1987 | Hall | 128/205.24 |
| 4,671,436 A * | 6/1987 | Hagan | 222/402.25 |
| 4,692,492 A * | 9/1987 | Gunesin | 524/731 |
| 5,133,701 A * | 7/1992 | Han | 604/289 |
| 5,318,019 A | 6/1994 | Celaya | 128/204.26 |
| 5,329,975 A * | 7/1994 | Heitel | 141/19 |
| 5,597,095 A * | 1/1997 | Ferrara, Jr. | 222/402.12 |
| 5,944,013 A | 8/1999 | Burch | 128/205.14 |
| 5,979,442 A | 11/1999 | Orr | 128/204.18 |
| 6,119,902 A * | 9/2000 | Shimada et al. | 222/321.3 |
| 6,145,503 A * | 11/2000 | Smith | 128/202.16 |
| 6,338,442 B1 * | 1/2002 | De Laforcade | 239/337 |
| 6,398,082 B2 * | 6/2002 | Clark et al. | 222/402.11 |
| 6,494,201 B1 | 12/2002 | Welik | 128/200.23 |
| 6,510,847 B1 * | 1/2003 | Helgesson et al. | 128/200.23 |
| 6,708,692 B2 | 3/2004 | Lee et al. | 128/205.24 |
| 6,851,626 B2 * | 2/2005 | Patel et al. | 239/338 |

(Continued)

*Primary Examiner*—Justine R. Yu
*Assistant Examiner*—Shumaya B. Ali
(74) *Attorney, Agent, or Firm*—Blackwell Sanders LLP

(57) ABSTRACT

A portable oxygen supply unit for breathable air with an enhanced oxygen content has a tilt valve in a mounting cup on a pressurized container containing medical or aviators oxygen. A hollow housing is sealed to the mounting cup. The hollow housing is flowably connected to a mouthpiece and to an inlet for ambient air. A user can open the tilt valve with an actuator that is slidable in the hollow housing. When the valve is open, the pressurized oxygen flows into the hollow housing. As the user inhales through the mouthpiece the oxygen released from the container is diluted with ambient air drawn through the inlet for efficient use of the oxygen dispensed from the container.

20 Claims, 5 Drawing Sheets

U.S. PATENT DOCUMENTS

| | | | |
|---|---|---|---|
| 6,874,663 B2 * | 4/2005 | Scheindel | 222/402.15 |
| 7,051,731 B1 * | 5/2006 | Rogerson | 128/200.23 |
| 7,056,494 B2 * | 6/2006 | Adjei et al. | 424/45 |
| 7,204,393 B2 * | 4/2007 | Strand | 222/402.13 |
| 7,225,805 B2 * | 6/2007 | Bacon | 128/200.23 |
| 7,249,692 B2 * | 7/2007 | Walters et al. | 222/153.11 |
| 2002/0148465 A1 * | 10/2002 | Sealfon | 128/200.24 |
| 2004/0094157 A1 | 5/2004 | Dantanarayana et al. | 128/206.21 |
| 2005/0081849 A1 | 4/2005 | Warren | 128/201.22 |

* cited by examiner

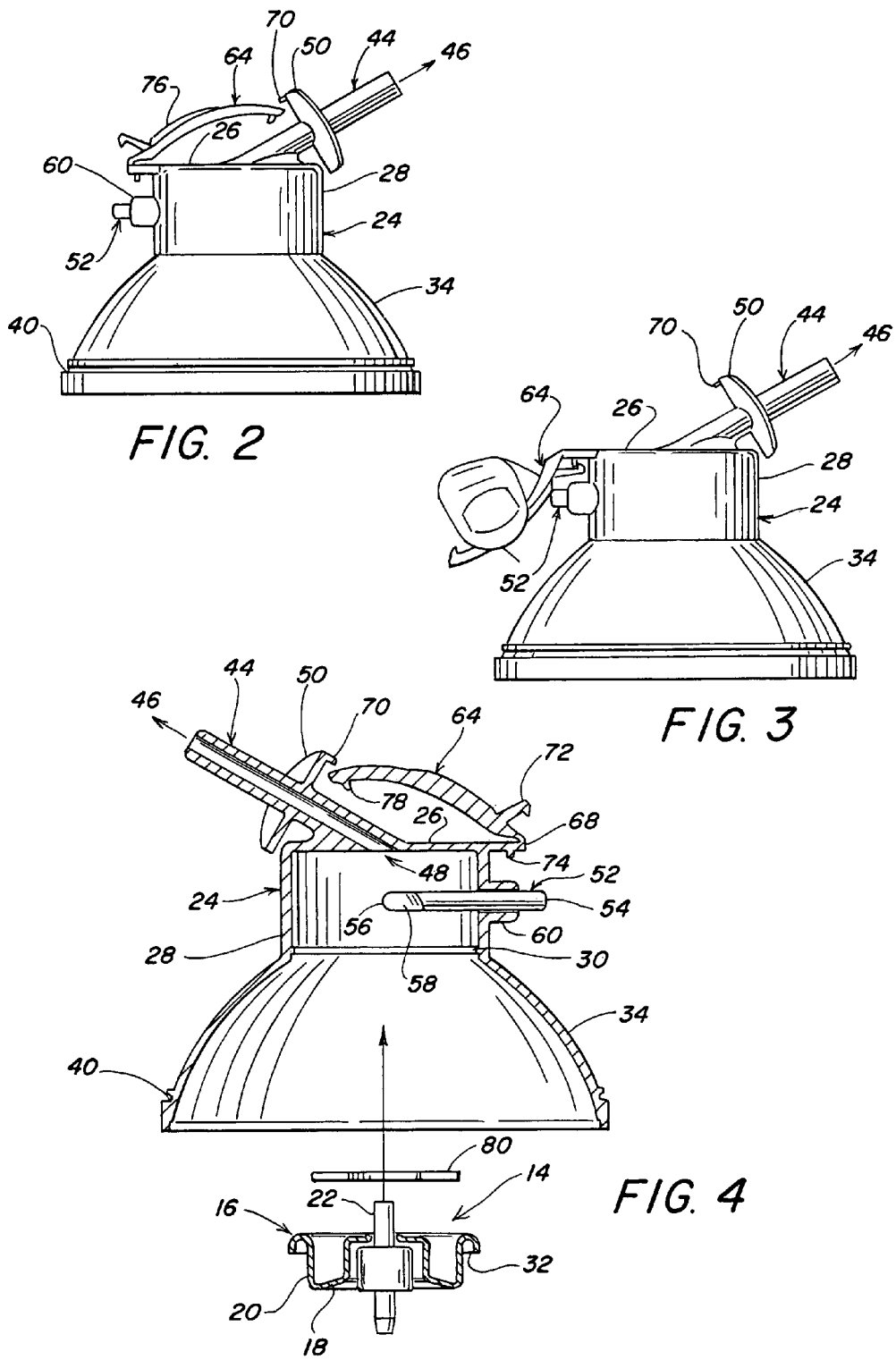

PORTABLE OXYGEN SUPPLY UNIT

BACKGROUND OF THE INVENTION

1. Field of the Invention

The present invention relates to a portable oxygen supply unit for delivering breathable air with enhanced oxygen content.

2. Brief Description of the Prior Art

Ambient air contains about twenty percent by weight oxygen with the balance being mainly nitrogen. It is known that breathing air with a higher oxygen content has beneficial effects on persons such as athletes, aviators and sportsmen to allay respiratory exertion, on persons suffering from asthma or other respiratory ailments, and those temporarily suffused with certain poisons, fumes, smoke or an excess of alcohol. Many other conditions such as altitude sickness and migraines also benefit from treatment with oxygen. In addition to these uses, as air quality declines because of pollution and the oxygen content in the air declines because of deforestation, others may find temporarily breathing oxygen enriched air beneficial in today's stress-ridden, fast-paced world where peak performance is expected at all times. A little extra oxygen can promote increased alertness and physical stamina.

Oxygen which is suitable for human use, i.e., aviators and medical oxygen, is typically stored in cylinders. The oxygen is piped through tubes and administered through a mask or nose-piece. Medical oxygen is administered by prescription; aviators oxygen is available to the public. There are commercial locations called oxygen bars that provide customers with an opportunity to temporarily inhale breathable air that contains a higher concentration of oxygen. Currently customers of these establishments use a small flexible hose called a cannula or mask to deliver the oxygen-enriched breathable air into the nostrils.

When a person needs an oxygen lift and is not on prescription oxygen, a commercial facility may not exit or may not be open. Nor is keeping a personal oxygen cylinder practical as, absent a cart such as used by an emphysema patient, oxygen cylinders are not portable. Moreover, the tubing, mask and nose-piece arrangement used with oxygen cylinders is unattractive as it is associated with being sick. It is also cumbersome and not transportable. What is needed is an oxygen supply unit that is portable, preferably relatively inexpensive, and does not use tubes, masks or nose-pieces. Such a product can also be filled with medical oxygen and sold by prescription for example in the treatment of migraines and other non-life threatening conditions which require a small amount of oxygen for treatment.

BRIEF SUMMARY OF THE INVENTION

In view of the above, it is an object of the present invention to provide a portable oxygen supply unit for use in administering medical or aviators oxygen efficiently without the need for cannula, masks or nose-pieces. It is another object to provide a supply unit for administering breathable air with an enhanced oxygen content and an aroma. Other objects and features of the invention will be in part apparent and in part pointed out hereinafter.

In accordance with the invention, a portable oxygen supply unit for delivering breathable air with enhanced oxygen content in major part has:

a mouthpiece with an air discharge opening and an air intake opening, a hollow housing, said air intake opening of the mouthpiece flowably connected to the hollow housing, at least one inlet in the hollow housing flowably connected to ambient air, a tilt valve with a stem extending above a mounting cup, said tilt valve sealed to the hollow housing by the mounting cup, a container for a pressurized gas having an oxygen content exceeding ambient air, said container sealed to the tilt valve by the mounting cup, an actuator slidable through a sidewall of the hollow housing for applying a lateral force to the stem of the tilt valve to open the tilt valve and allow the pressurized gas in the container to flow through the stem into the hollow housing. In use, the pressurized gas discharged through the tilt valve into the hollow chamber is mixed with ambient air inducted through the at least one inlet in the hollow chamber when a user inhales through the mouthpiece.

In some embodiments, a blotter with a scent is placed on the mounting cup of the tilt valve for emitting an aroma into the air in the hollow housing. This design places the scent outside the oxygen container in an airtight compartment to prevent the scent from oxidizing. In some embodiments a finger pad on the actuator allows a user to apply manual pressure to the tilt valve. Other embodiments make use of a trigger pivoted to the housing for operating the actuator. A common theme to these and other various embodiments hereinafter described is the efficient use of oxygen dispensed from the container.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 2 is a side elevation of a hollow housing portion of the supply unit with an attached mouthpiece and with a trigger for operating the actuator shown in a storage position;

FIG. 3 is a side elevation of the hollow housing with the trigger shown in a use position;

FIG. 4 is an exploded cross-section of the hollow housing showing a tilt valve in a mounting cup and a blotter for a scent;

DETAILED DESCRIPTION OF THE INVENTION

Figure 1:
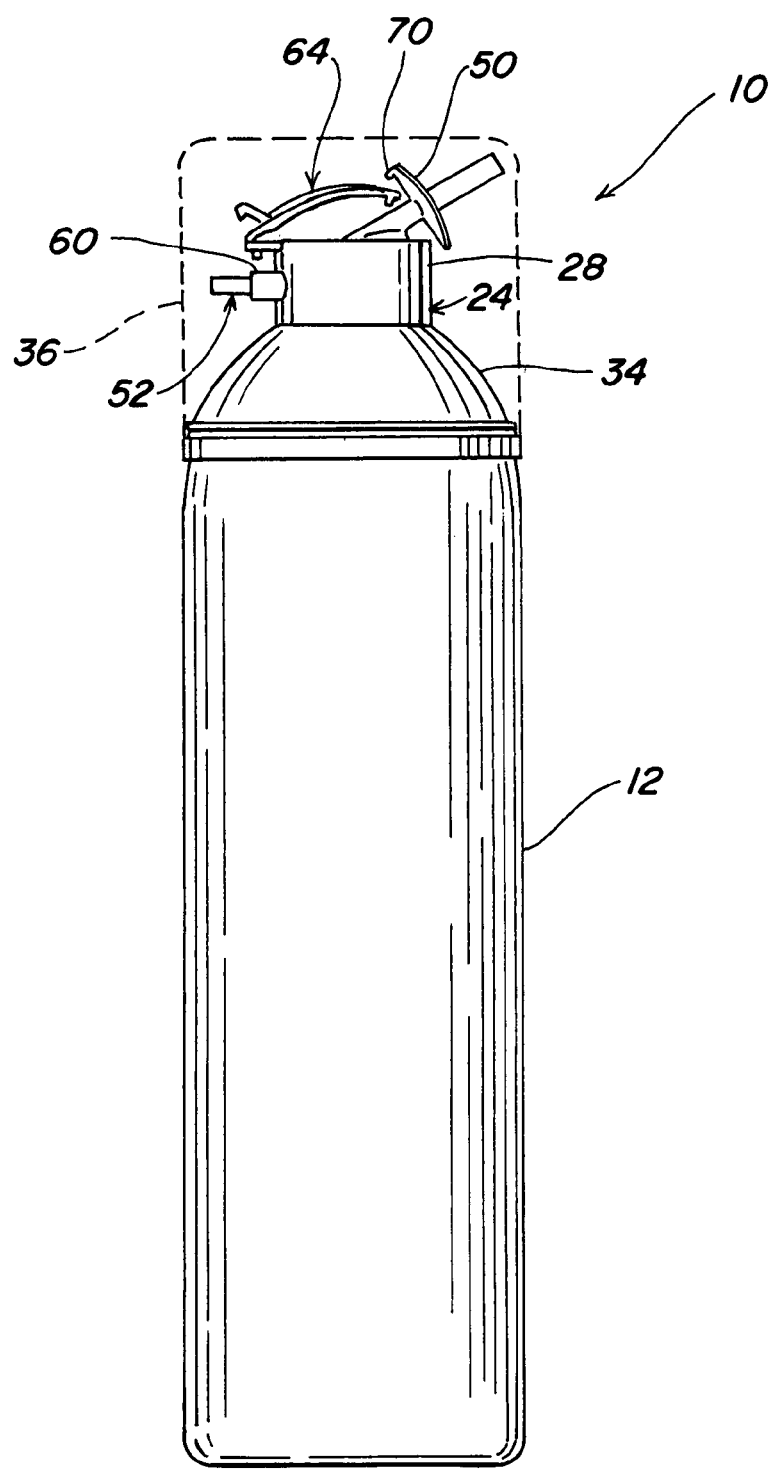
FIG. 1 is a side elevation of a portable oxygen supply unit in accordance with the present invention; a cap is shown in broken lines.

Referring to the drawings more particularly by reference character and starting with FIG. 1, reference numeral 10 refers to a portable oxygen supply unit in accordance with the present invention. Supply unit 10 includes a container 12 for pressurized gas. Container 12 may be of a conventional type having a discharge orifice sealed to a tilt valve 14 (FIG. 4). The body wall of container 12 is of a gage suitable to contain the compressed gas under the required pressure, and is preferably made of an aluminum alloy or plastic, to keep its weight to a minimum, for ease in handling and shipping. Container 12 may be sized such that it is easily held in the hand, for example be six to ten inches in height and two to four inches in diameter. In the form illustrated, container 12 is cylindrical in shape but it may take various other shapes in cross-section.

Tilt valve 14 includes a mounting cup 16. Mounting cup 16 is formed with an integral substantially flat circular bottom 18 and a peripheral skirt 20 shaped to receive a bead of container 12 in a conventional manner and sealing tilt valve 14 to container 12. A hollow stem 22 of tilt valve 14 extends both above and below mounting cup 16. When a lateral force is applied to hollow stem 22 above mounting cup 16 (i.e., the valve is tilted), pressurized gas flows from container 12 and out hollow stem 22 in a conventional manner. When pressure on stem 22 is released, a spring (not shown) causes tilt valve 14 to return to its closed position in a conventional manner.

With continuing reference to FIG. 4, mounting cup 16 is also sealed to a hollow housing 24. In the form illustrated, hollow housing 24 is cylindrical in shape but it may take other shapes. Hollow housing 24 has a top wall 26 and a sidewall 28 by means of which housing 24 is sealed to mounting cup 16. The sealing means may comprise a circumferential ridge 30 (FIGS. 46 and 10) formed on the inside of sidewall 28. As illustrated, ridge 30 is near an end of sidewall 28 opposite top wall 26 and is adapted to snap under a free end 32 (FIG. 4) of peripheral skirt 20 forming an airtight seal and connecting hollow housing 24 to mounting cup 16.

In the embodiment shown in FIGS. 1-8, a depending skirt 34 may be attached or integrally formed with sidewall 28 of hollow housing 24. Depending skirt 34 forms a hood over an upper end of container 12 below tilt valve 14. When supply unit 10 includes a cap 36, an airtight seal may be formed between cap 36 and depending skirt 34. As illustrated in the drawings (FIGS. 4-5), suitable sealing means may comprise a bead 38 on the inside of cap 36 which is received in a channel 40 provided for that purpose in depending skirt 34. Multiples of these elements and other arrangements as will occur to those skilled in the art are included within the present disclosure.

One or more inlets 42 (FIGS. 7-8 and 11) for admitting ambient air into hollow housing 24 are provided. Inlets 42 may take the form of holes formed in top wall 26 although they may be located in sidewall 28 if desired. Some or all of inlets 42 may include a filter for filtering all or some part of the air inducted into hollow housing 24.

A mouthpiece 44 with an air discharge opening 46 is attached to hollow housing 24 through an air intake opening 48. Mouthpiece 44 may be attached to top wall 26 of hollow chamber 24 and positioned such that air discharge opening 46 is angled towards a user. Air discharge opening 46 may be flattened so that it may be comfortably gripped between the user's teeth and may include a flange 50 against which the user's lips may be sealed.

Figure 5:
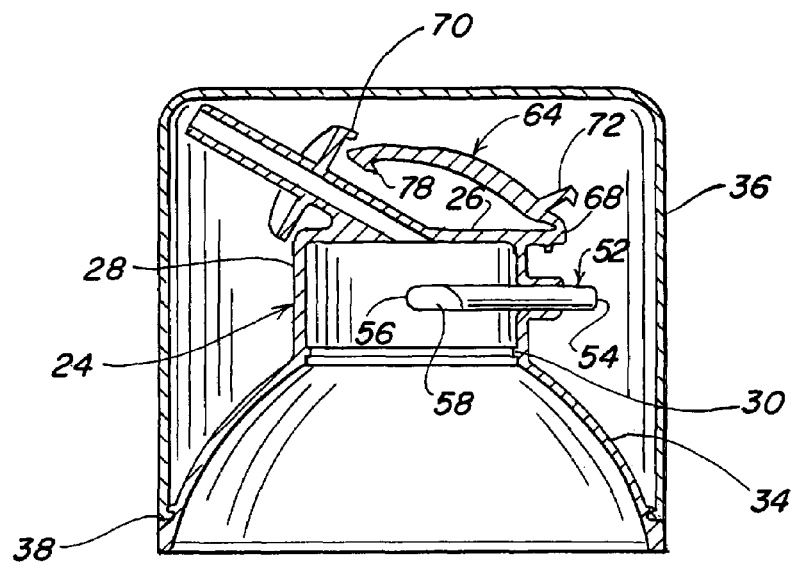
FIG. 5 is a cross-section of the hollow housing with the trigger in storage position and the cap sealed to a depending skirt attached to the hollow housing.
Figure 6:
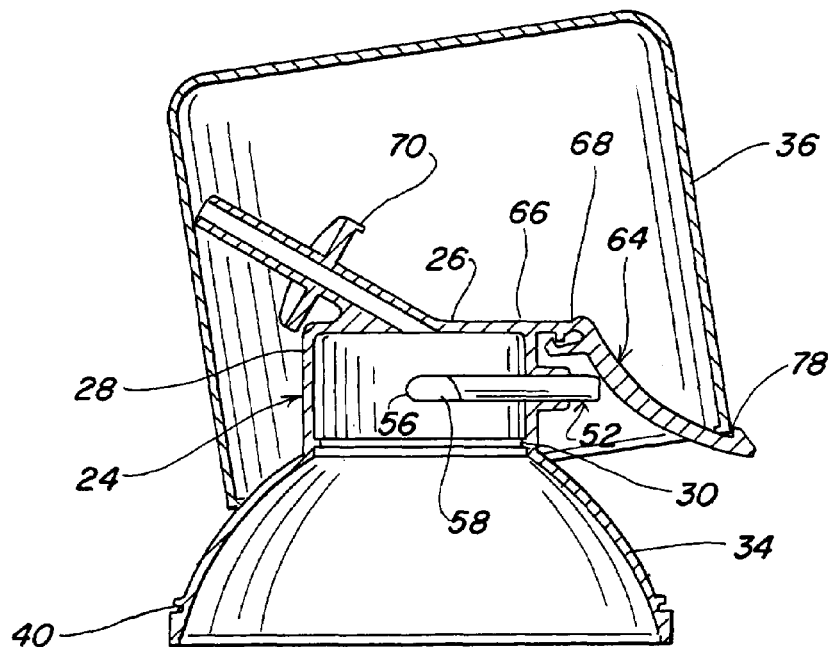
FIG. 6 is a cross-section of the hollow housing with the trigger in use position illustrating how a projection on the trigger prevents the cap from sealing to the depending skirt.
Figure 7:
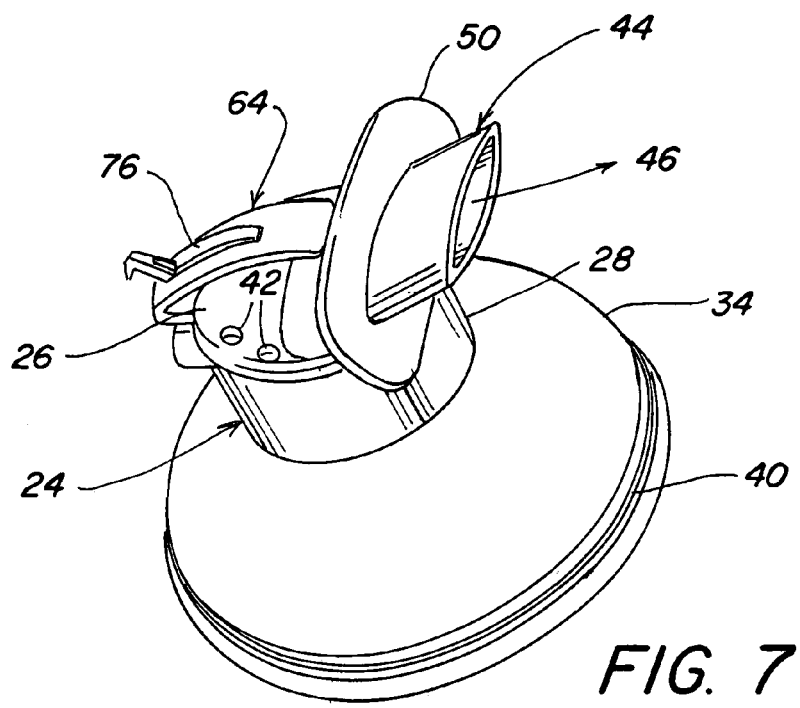
FIG. 7 is a perspective view of the hollow housing as viewed from above.
Figure 8:
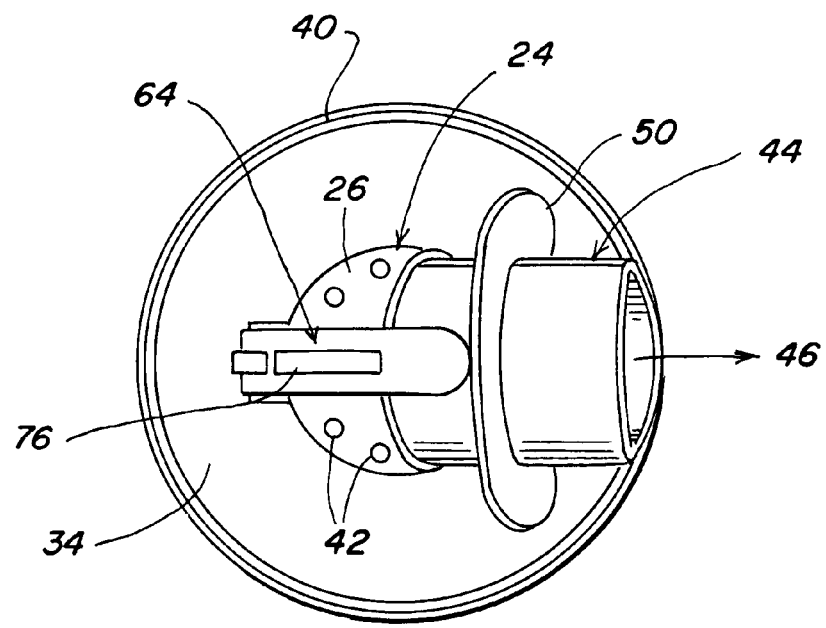
FIG. 8 is a plan view of the hollow housing as viewed from above.
Figure 9:
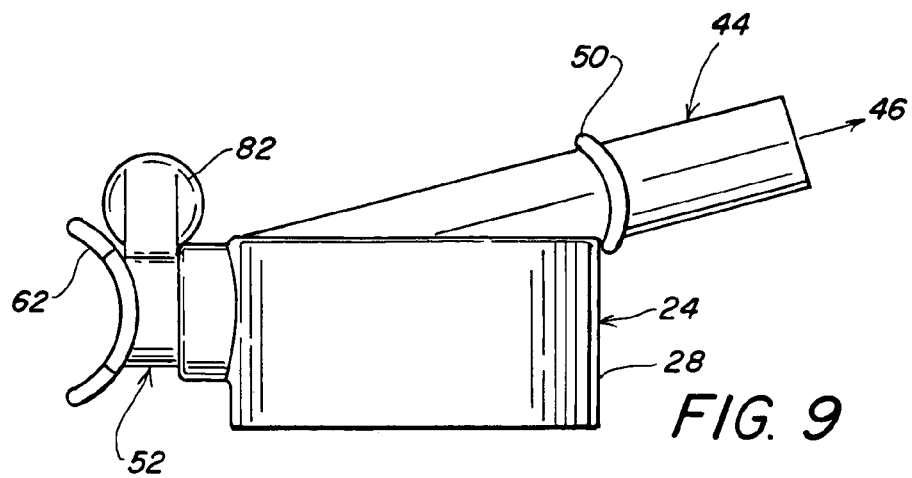
FIG. 9 is a side elevation of a hollow housing with a finger pad for operating the actuator.
Figure 10:
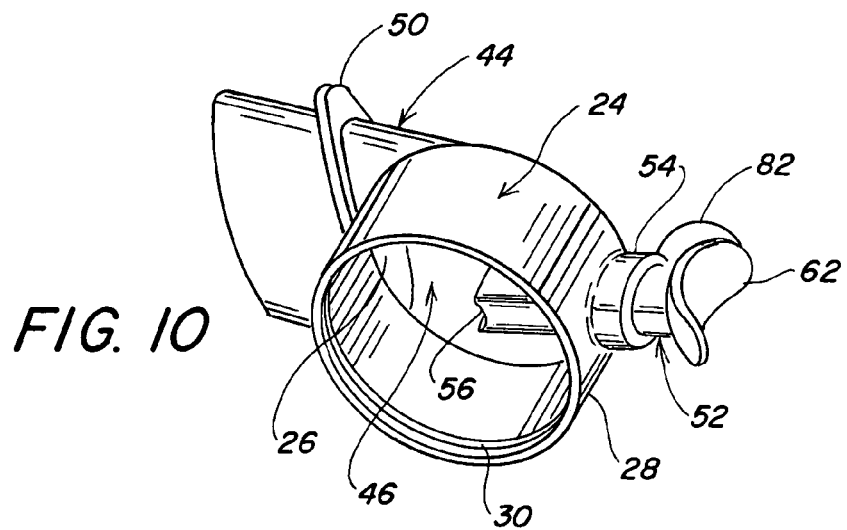
FIG. 10 is perspective view of the hollow housing shown in FIG. 9 viewed from below; and, FIG. 11 is a perspective of the hollow housing shown in FIG. 9 viewed from above.

An actuator 52 for applying a lateral force to stem 22 of tilt valve 14 is provided. Actuator 52 may be an elongated flat bar, a heel 54 of which is flat and a toe 56 of which is arcuate. Arcuate toe 56 may be beveled 58 as shown (FIGS. 4-6). Actuator 52 passes through an aperture provided in sidewall 28 of hollow housing 24. A hollow guideway 60 may be provided on the inside or outside of sidewall 28 for the purpose of supporting actuator 52 as it is reciprocated in the aperture. A pad 62 which may be curved to conform to the shape of a finger may be attached to heel 54 of actuator 52 as shown in FIGS. 9-10 or as shown in FIGS. 1-8, actuator 52 may be operated with a trigger 64.

Trigger 64 may be pivoted to a strap 66 attached to hollow housing 24 above guideway 60 as shown. The pivot 68 may be a separate element or when strap and trigger are integrally formed as by molding, pivot 68 may be a self-hinge. Before supply unit 10 is used or during storage between uses, trigger 64 is pivoted upwardly. Flange 50 may be provided with a catch 70 under which a leading end of trigger 64 may be caught. When trigger 64 is used to operate actuator 52, trigger 64 is pivoted about pivot 68 into the position shown in FIG. 3. Trigger 64 may be provided with a hook 72 (FIGS. 4-6) which snaps over a finger 74 provided on an underside of strap 66 for retaining trigger 64 in ready position to operate actuator 52. An underside of trigger 64 may also be provided with a longitudinal reinforcing rib 76 (FIGS. 2 and 7-8). The outside of trigger 64 at its free end may be provided with a projection 78 (FIGS. 4-6) for use as described hereinafter.

A pressure gauge may be connected to container 12 to allow the user to check the remaining amount of oxygen in supply unit 10. Gauge may be calibrated to show the actual pressure in container 12 or may be a simple scale ranging between "empty" and "full" with a needle indicator and so forth.

In use, tilt valve 14 is installed on container 12 and container 12 filled with a breathable air with enhanced oxygen content to a relatively low superatmospheric pressure. Preferably commercially available aviators or medical oxygen is used. Good results have been obtained when container 12 is filled with 150 to 180 pounds/square inch of pressure although container 12 may be filled with more or less breathable air with enhanced oxygen content if desired.

If it desired to add an aroma to the breathable air with enhanced oxygen content, a blotter 80 (FIG. 4) may be dipped, sprayed or otherwise impregnated with a scent. Blotter 80 may be a disk designed to fit over stem 22 of tilt valve 14 and be seated on bottom wall 18 of mounting cup 16.

After blotter 80, if any, is installed in mounting cup 16, hollow housing 24 is slipped over mounting cup 16 until ridge 30 snaps under free end 32 of peripheral skirt 20 forming an airtight seal and connecting housing 24 to mounting cup 16. In starting position for the embodiment shown in FIGS. 1-8, trigger 64 is pivoted upwardly about pivot 68 and the free end is caught under catch 70 provided on flange 50 of mouthpiece 44. Cap 36 is slipped over hollow housing 24 until bead 38 is seated in channel 40 provided in depending skirt 34 of hollow housing 24 forming an airtight seal.

If an aroma is applied to blotter 80, loss of odor on standing is minimal due to either oxidation or escape with supply unit capped. While the aroma may vaporize from blotter 80 into hollow housing 24 and through mouthpiece 44 and inlets 42 into the space between the outside of hollow housing 24 and cap 36, it cannot escape into the atmosphere because of the airtight seal between cap 36 and depending skirt 34 of hollow housing 24. As those skilled in the art will recognize, the term "airtight" means substantially airtight, not necessarily absolutely airtight. Equilibrium is thus reached and evaporation of additional scent stayed.

When a user needs an oxygen lift and when supply unit 10 is as shown in FIGS. 1-8, cap 36 is removed and trigger 64 rotated about pivot 68 until hook 72 snaps under finger 74 on strap 66. Finger pressure on trigger 64 causes actuator 52 to slide in guideway 60 until toe 56 contacts stem 22 of tilt valve 14. Further pressure on trigger 64 causes toe 56 to tilt stem 22 and pressured breathable air with enhanced oxygen content flows from container 12 into hollow housing 24. As the pressurized gas is released into hollow housing 24, the user places his or her mouth around mouthpiece 44 and inhales through the mouthpiece. When the volume of air inhaled is larger than the volume of pressurized gas released into hollow housing 24, ambient air is drawn through inlets 42, mixed with the breathable air with enhanced oxygen content and passes into the user's lungs through air discharge opening 46. For medicinal purposes, it may be preferred if the dilution is in the order of 60/40 (i.e., 60 parts oxygen, 40 parts ambient air) but for other purposes, a dilution of 40/60 may be preferred. If mixing with ambient air did not occur, more pressurized gas from container 12 would need to be released from container 12 to fill the user's lungs. This would be a waste of product as the user's lungs would not be able to absorb all of the oxygen. By blending pure oxygen from container 12 with ambient air from air inlet 42 in hollow housing 24, the oxygen content of the breathable air inhaled through mouthpiece 44 may be optimized to that amount that the hemoglobin in the lungs can absorb for efficient use of the oxygen dispensed from container 12. Between breaths, pressure on trigger 64 is released, the spring in tilt valve 14 causes the valve to return to closed position. As stem 22 is righted, actuator 52 is reciprocated back into starting position.

With aviators oxygen and a dilution of 60/40, good results (e.g., increased alertness and physical stamina) may be obtained by taking 30-40 breaths when container 12 is pressured to 150-180 pounds and contains 5 to 10 grams of pure oxygen which at atmospheric pressure occupies a volume of 10 to 12 liters. For the treatment of migraines, altitude sickness or for use under emergency conditions, such as in a smoke filled room or fuselage, and so forth, the number of breaths and the spacing of breaths may vary.

If container 12 is not empty at the end of a treatment session, trigger 64 may be rotated back into stored position and cap 36 reinstalled on depending skirt 34. When pivot 68 is a self hinge, movement of trigger 64 about pivot 68 causes a color change in the plastic thus indicating that supply unit 10 has been used by another person. If the user forgets to position trigger 64 in stored position, projection 78 prevents cap 36 from being reinstalled causing trigger 64 to open tilt valve 14 and waste the oxygen.

Figure 11:
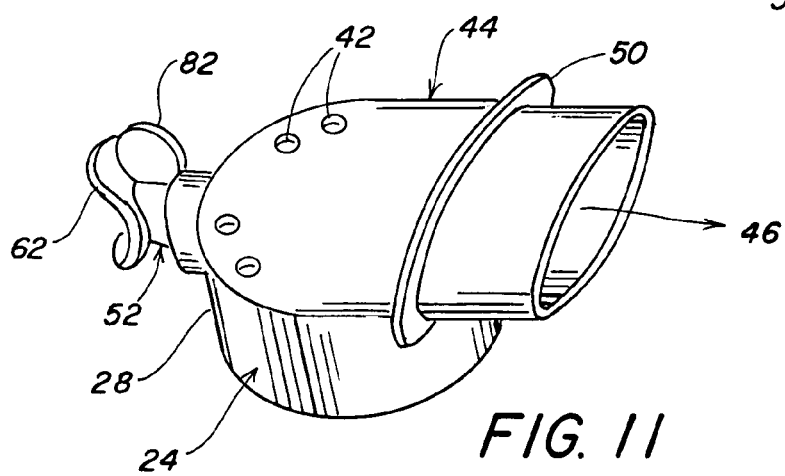

Operation of the embodiment shown in FIGS. 9-11 is similar to that of FIGS. 1-8 except that actuator 52 is manually operated with pad 62. A tear off tab 82 which when removed signals that the supply unit has been used or tampered with.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A portable oxygen supply unit for delivering breathable air with enhanced oxygen content comprising a container for pressurized gas, a mouthpiece with an air discharge opening and an air intake opening, a cylindrically shaped hollow housing with a top wall and a sidewall, said air intake opening of the mouthpiece fluidly connected to the top wall of the hollow housing, at least one inlet in the hollow housing flowably connected to ambient air, said sidewall having a circumferential ridge on the inside of the hollow housing, said sidewall having a depending skirt that forms a hood over an upper end of the container, a tilt valve with a stem extending above a mounting cup, said mounting cup having a bottom wall and a peripheral skirt with a free end under which the ridge of the sidewall of the hollow housing is snapped to form an airtight seal between the hollow housing and the mounting cup, said container for a pressurized gas having an oxygen content exceeding ambient air, said container sealed to the tilt valve by the mounting cup, an actuator slidable through a sidewall of the hollow housing for applying a lateral force to the stem of the tilt valve to open the tilt valve and allow the pressurized gas in the container to flow through the stem into the hollow housing, a cap, and means for forming an airtight seal between the cap and the depending skirt of the hollow housing, whereby the pressurized gas discharged through the tilt valve into the hollow chamber is mixed with ambient air inducted through the at least one inlet in the hollow chamber when a user inhales through the mouthpiece.

2. The supply unit of claim 1 further comprising a blotter placed on the bottom of the mounting cup, said blotter impregnated with a scent for adding an aroma to the breathable air.

3. The supply unit of claim 1 wherein the actuator is an elongated flat bar with an arcuate toe that is beveled on the underside, said supply unit further comprising a hollow guideway on the sidewall for the actuator.

4. The supply unit of claim 1 wherein a trigger is pivoted on the sidewall above the guideway.

5. The supply unit of claim 4 wherein the mouthpiece has a flange against which a user's lips is adapted to be sealed, said flange having a catch under which a leading end of the trigger is caught when the trigger is in a storage position.

6. The supply unit of claim 1 wherein a trigger is pivoted from a strap attached to the sidewall above the guideway.

7. The supply unit of claim 6 wherein the trigger has a hook which snaps over a finger provided on the underside of the strap for retaining the trigger in a use position to operate the actuator.

8. The supply unit of claim 7 wherein the trigger has a projection at a free end for preventing the cap from sealing to the depending skirt when the trigger is in the use position.

9. The supply unit of claim 1 wherein the mouthpiece is attached to the top wall of the hollow chamber and is positioned such that the air discharge opening is angled towards a user and is flattened such that it is adapted to be comfortably gripped between a user's teeth and lips.

10. The supply unit of claim 1 wherein the pressurized gas released into the hollow housing is diluted with ambient air draw through the air inlet in a ratio between about 40/60 parts by volume and about 60/40 parts by volume when a user inhales through the mouthpiece.

11. The supply unit of claim 10 wherein the air inlet comprises a plurality of holes in the top wall of the hollow housing.

12. A portable oxygen supply unit for delivering breathable air with enhanced oxygen content comprising
   a mouthpiece with an air discharge opening and an air intake opening,
   a hollow housing, said air intake opening of the mouthpiece is fluidly connected to the hollow housing, at least one inlet in the hollow housing is fluidly connected to ambient air,
   a tilt valve with a stem extending above a mounting cup, said tilt valve sealed to the hollow housing by the mounting cup,
   a container for a pressurized gas having an oxygen content exceeding ambient air, said container sealed to the tilt valve by the mounting cup,
   an actuator slidable through a sidewall of the hollow housing for applying a lateral force to the stem of the tilt valve to open the tilt valve and allow the pressurized gas in the container to flow through the stem into the hollow housing,
   whereby the pressurized gas discharged through the tilt valve into the hollow chamber is mixed with ambient air inducted through the at least one inlet in the hollow chamber when a user inhales through the mouthpiece.

13. The supply unit of claim 12 wherein the hollow housing has a top and a sidewall with a depending skirt that forms a hood over an upper end of the container below the tilt valve.

14. The supply unit of claim 13 further comprising a cap and means for forming an airtight seal between the cap and the depending skirt.

15. The supply unit of claim 14 wherein the tilt valve has a flat circular bottom on which a blotter with a scent is placed for adding an aroma to the breathable air.

16. A portable oxygen supply unit for delivering breathable air with enhanced oxygen content comprising
   a mouthpiece with an air discharge opening and an air intake opening,
   a cylindrically shaped hollow housing with a top wall and a sidewall, said air intake opening of the mouthpiece is fluidly connected to the top wall of the hollow housing, at least one inlet in the hollow housing is fluidly connected to ambient air, said sidewall having a circumferential ridge on the inside of the hollow housing,
   a tilt valve with a stem extending above a mounting cup, said mounting cup having a peripheral skirt with a free end under which the ridge of the sidewall of the hollow housing is snapped to form an airtight seal between the hollow housing and the mounting cup,
   a container for a pressurized gas having an oxygen content exceeding ambient air, said container sealed to the tilt valve by the mounting cup,
   an actuator slidable through a sidewall of the hollow housing for applying a lateral force to the stem of the tilt valve to open the tilt valve and allow the pressurized gas in the container to flow through the stem into the hollow housing,
   whereby the pressurized gas discharged through the tilt valve into the hollow chamber is mixed with ambient air inducted through the at least one inlet in the hollow chamber when a user inhales through the mouthpiece.

17. The supply unit of claim 16 wherein the actuator is an elongated flat bar with an arcuate toe that is beveled on the underside.

18. The supply unit of claim 17 further comprising a hollow guideway for the actuator.

19. The supply unit of claim 18 wherein the actuator has a heel with finger pad by means of which the actuator is reciprocated in the guideway.

20. The supply unit of claim 18 wherein the actuator is reciprocated in the guideway with a trigger pivoted on the sidewall on the hollow housing above the guideway.

* * * * *